United States Patent [19]

Fukuhara

[11] Patent Number: 5,541,156

[45] Date of Patent: Jul. 30, 1996

[54] PROTEIN

[75] Inventor: Toshihiko Fukuhara, Kiyose, Japan

[73] Assignees: Mitsubishi Corporation; Mitsubishi Kasei Corporation, both of Tokyo, Japan

[21] Appl. No.: 341,042

[22] Filed: Nov. 15, 1994

Related U.S. Application Data

[63] Continuation of Ser. No. 74,492, Jun. 11, 1993, abandoned.

[30] Foreign Application Priority Data

Jun. 11, 1992 [JP] Japan .................................. 4-177388

[51] Int. Cl.$^6$ .......................... A01N 37/18; A01N 63/00; C07K 14/065
[52] U.S. Cl. .................... 514/2; 47/58; 530/350; 119/6.5
[58] Field of Search ................ 530/350, 388.3, 530/389.4, 826; 47/58; 119/6.5; 514/2; 424/204.1

[56] References Cited

PUBLICATIONS

Journal of Insect Pathology 1, pp. 215–231 (1959) Tanada et al. "Synergism between Two Viruses of the Armyworm, *Pseudaletia unipuncta*".

Journal of Invertebrate Pathology 17, pp. 116–126 (1971) Tanada et al. "Enhanced Infection of a Nuclear–Polyhedrosis Virus in larvae of the Armyworm, *Pseudaletia unipuncta*, by a Factor in the Capsule of a Granulosis Virus".

Journal of Invertebrate Pathology 27, pp. 115–124 (1976) Hara et al. "Isolation and Characterization of a Synergistic Enzyme from the capsule of a Granulosis Virus of the Armyworm, *Pseudaletia unipuncta*".

Journal of Invertebrate Pathology 31, pp. 48–56 (1978) Yamamoto et al. "Phospholipid, an Enhancing Component in the Synergistic Factor of a Granulosis Virus of the Armyworm, *Pseudaletia unipuncta*".

Journal of Invertebrate Pathology 54, pp. 49–56 (1989) Zhu et al. "Location of a Synergistic Factor in the Capsule of Granulosis Virus of the Armyworm, *Pseudaletia unipuncta*".

Virology 167, pp. 242–250 (1988) Derksen et al. "Alteration of a Lepidopteran Peritrophic Membrane by Baculoviruses and Enhancement of Viral Infectivity".

Journal of General Virology 72, pp. 2645–2651 (1991) Hashimoto et al. "Location and nucleotide sequence of the gene encoding the viral enhancing factor of the *Trichoplusia ni* granulosis virus".

Virology 175, pp. 427–433 (1990) Yuen et al. "Identification and Sequencing of the Spheroidin Gene of *Choristoneura biennis* Entomopoxvirus".

Shimamura et al., Applied Entomology & Zoology, vol. 23(4), pp. 396–400, 1988.

*Primary Examiner*—Mary E. Mosher
*Assistant Examiner*—Laurie Scheiner
*Attorney, Agent, or Firm*—Wenderoth, Lind & Ponack

[57] ABSTRACT

Novel protein having the following physicochemical properties was purified from the occlusion body of entomopoxvirus:

(1) it has a molecular weight of 38,000 on SDS polyacrylamide gel, (2) it has an isoelectric point of 3.8, (3) it is stable in the pH range of 5.5–11.0, (4) it is stable at temperature up to 75° C., and (5) it enhances the infection of nuclear polyhedrosis virus. Since the novel protein of the present invention has an activity to enhance the infection of nuclear polyhedrosis virus, it provides economical biopesticides in combination with the virus solution.

2 Claims, 2 Drawing Sheets

PROTEIN

This application is a continuation of now abandoned application, Ser. No. 08/074,492, filed Jun. 11, 1993.

The present invention relates to a novel protein. More particularly, this invention relates to a novel protein which enhances the susceptibility of insects, or cell lines derived from the insects, to infection by nuclear polyhedrosis viruses.

There has recently been developed a method to control harmful insects by artificially allowing an entomopathogenic virus to prevail among various harmful insects, which is so-called biopesticide. More specifically, the method comprises sprinkling such virus on plants to be eaten by harmful insects, which allows the insects orally to take it and to be infected with the virus, and further allows other insects to be infected with the virus, which generates an infection cycle. The virus to be sprinkled is collected and purified from orally inoculated insects which had been cultivated on a large scale.

Of entomopathogenic viruses, nuclear polyhedrosis virus shows high host specificity. The hosts are limited to arthropods such as insect, shrimp or the like. Since the nuclear polyhedrosis virus is considered to be a safe biopesticide, harmless to organisms other than the above-noted target hosts, utilization of this virus for the control of harmful insects has been promoted.

On the other hand, the control of harmful insects by nuclear polyhedrosis virus has a big problem for practical use because of the high cost performance and different application method compared with chemical insecticides. Accordingly, an attempt has been done to reduce the amount of nuclear polyhedrosis virus to be sprinkled per unit area by adding some infection-enhancing factors to the virus, which leads to the reduction of the cost of biopesticides.

Study of the infection-enhancing factor was initiated, starting from the study of interaction between two kinds of Baculoviridae, namely nuclear polyhedrosis virus and granulosis virus. Diseases caused by these viruses are characterized by forming an "occlusion body" in an infected cell, which encloses virus particles. The occlusion body of the nuclear polyhedrosis is called a polyhedra, and the occlusion body of granulosis is called a capsul. Determination of the infection-enhancing activity consists of orally administering a mixture of an agent and a solution containing nuclear polyhedrosis virus to a larvae and examining the onset of the disease for about 2 weeks thereafter. When the enhancing activity of the agent is positive, the onset ratio raises by adding the agent. For determining quantitatively this enhancing activity, there is adopted a method of comparing the amount of nuclear polyhedrosis virus necessary for inducing, for example, 50% infection (50% infectious amount) with that obtained when no agent is added. When the agent has such enhancing activity, 50% infectious amount should become lower by adding the agent. Thus, if the agent has 10-fold enhancing activity, the same onset ratio would be observed even if 1/10 virus is contained in the virus solution, when compared with a virus solution without the agent.

In 1959, Tanada reported in J. Insect Pathol. Vol. 1, pp.215–231, that the infection of nuclear polyhedrosis virus was enhanced markedly by oral inoculation to larvae of *Pseudalelia unipuncta* with a mixture of polyhedra of nuclear polyhedrosis virus of *P. unipuncta* (relative strain of armyworm) and a capsul of granulosis virus. In 1971, Tanada and Hukuhara reported in J. Invertebr. Pathol. Vol. 17, pp.116–126, that the above enhancement is attributed to a protein contained in the capsul. In 1976, Hara et al. reported in J. Invertebr. Pathol. Vol. 27, pp.115–124, that the protein was isolated by subjecting this capsul to gel filtration and hydroxyapatite column chromatography. In 1978, Yamamoto and Tanada reported in J. Invertebr. Pathol. Vol. 31, pp.48–56, that the infection-enhancing factor is a lipoprotein containing phospholipid and has a molecular weight of 126,000, and Zhu et al. reported in J. Invertebr. Pathol, Vol. 54, pp.49–56, that the lipoprotein has a molecular weight of 98,000.

In 1988, Derksen and Granados reported in Virology, Vol. 167, pp.242–250, that the occlusion body of granulosis virus of *Trichoplusia ni* contains a protein of molecular weight of 101,000 which enhances the infection of nuclear polyhedrosis virus. In 1991, Hashimoto et al. reported in J. General Virology, Vol. 72, pp.2645–2651, that they determined full length nucleotide sequence of the virus gene encoding this protein (VEF), and confirmed that the composition of the amino acids deduced from the nucleotide sequence is almost in accordance with the composition of the amino acids of the infection-enhancing factor originating from the granulosis virus of *P. unipuncta.*

As stated above, various information about the infection-enhancing factor of nuclear polyhedrosis virus has been accumulated, but an additional novel agent having the same function has been desired.

As a result of paying special attention to an entomopoxvirus, it has been found that such an infection-enhancing factor of nuclear polyhedrosis virus is contained in the occlusion body of the entomopoxvirus. The present invention has been established based on the findings.

Thus, the present invention is to provide a novel protein having the following physicochemical properties:

(1) it has a molecular weight of 38,000 on SDS polyacrylamide gel, (2) it has an isoelectric point of 3.8, (3) it is stable in the pH range of 5.5–11.0, (4) it is stable at temperature up to 75° C., (5) it enhances the infection of nuclear polyhedrosis viruses.

The present invention will be explained in detail below.

The protein of the present invention can be produced, for example, by extracting and purifying from the occlusion body of entomopoxvirus such as armyworm poxvirus. The entomopoxvirus is a subfamily of poxvirus family, to which double stranded DNA viruses whose host is an insect belong.

At first, an occlusion body of entomopoxvirus is produced. For example, entomopoxvirus is inoculated to larvae of army worm or a sensitive cell line thereof. When the poxvirus is to be inoculated to larvae, the feed previously contaminated with an occlusion body of the poxvirus is given to larvae so that the larvae take the feed into the digestive organ. Since the occlusion body is dissolved in digestive fluid and the virus particles contained therein are released, and the particles invade the sensitive tissues of the body and begin to grow, then cultivation of the larvae at 25°–30° C. will form the occlusion body within the infected tissues in 2–3 weeks. When the inoculation is made to the cell line, the sensitive tissues of infected larvae are aseptically taken out and added to the culture of the sensitive cell line, whereby the virus particles invade into the cells of the sensitive cell line and begin to grow. Cultivation of the cells at 25°–30° C. leads to formation of the occlusion body in the infected cells within 1–2 weeks. The supernatant of this infected cell culture contains virus and can be used as an inoculating source.

Then, the occlusion body is purified from the viruliferous larvae or infected cells. Specifically, viruliferous larvae or infected cells are pulverized with a homogenizer. The homogenized solution is filtrated through gauze or the like to remove cell debris, and washed by means of fractional centrifugation. The precipitate is suspended in a neutral buffer solution containing a detergent, subjected to ultrasonication to detach the cell ingredients attached to the occlusion body and washed by fractional centrifugation with distilled water. For removing remaining impurities, the washed occlusion body was overlayed on and subjected to the density gradient centrifugation such as sucrose, Parcol or the like, forming a band comprising the occlusion body. The band is collected, washed by fractional centrifugation with a neutral buffer solution, and the medium used for the density gradient was removed to give the purified occlusion body.

Infection-enhancing factor can be separated and purified from the purified occlusion body. For example, the purified occlusion body is treated with an alkaline solution containing a reductant to dissolve at first the crystalline protein constituting the occlusion body, thereby hardly soluble virus particles remain undissolved. The virus particles are removed by high speed centrifugation. The supernatant is subjected to gel filtration using Sephacryl column chromatography, and then hydroxyapatite column chromatography or the like, to give the infection-enhancing factor of the present invention.

Figure 3:
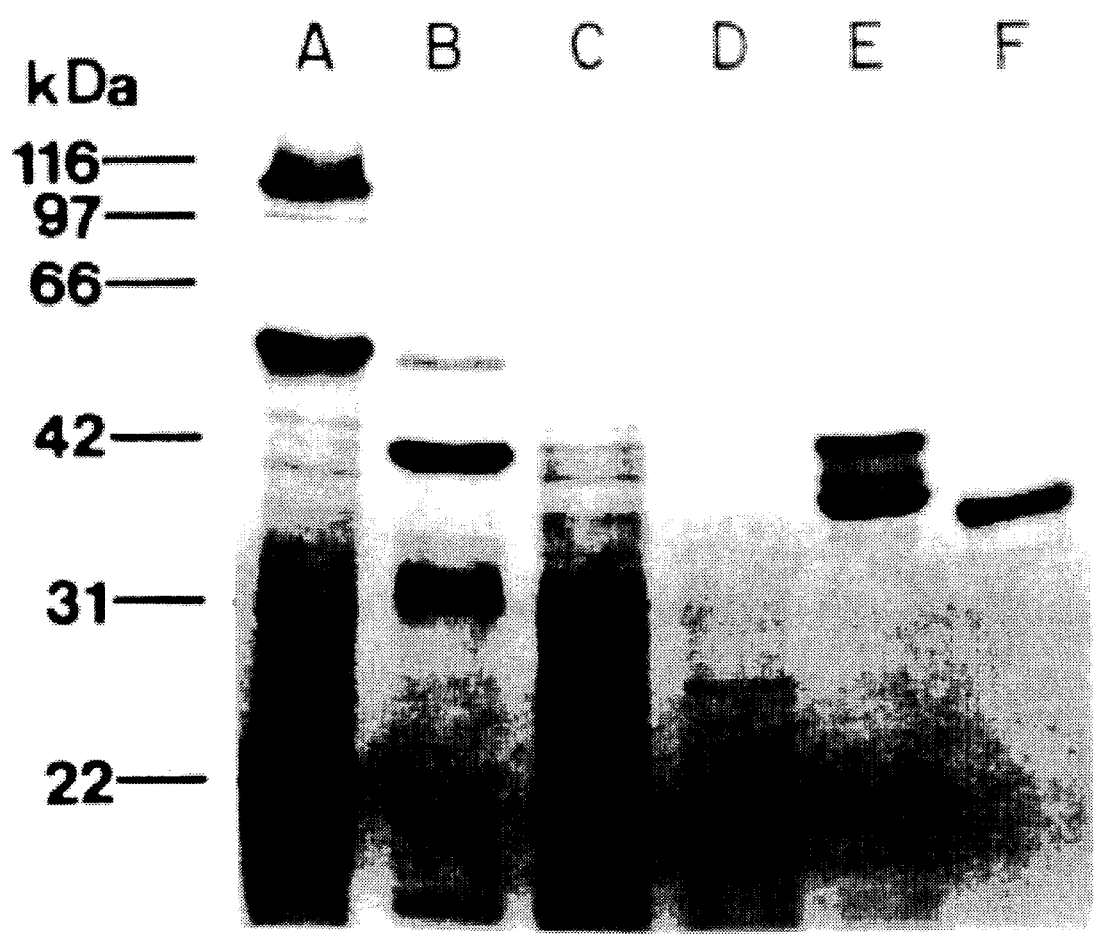

FIG. 3 shows SDS polyacrylamide gel electrophoresis of the agent of the present invention. Lane A represents the occlusion body, Lane B represents the body after alkali-treatment, Lane C represents army worm poxvirus granule itself, Lane D represents the granule after alkali-treatment, Lane E represents 2nd Fraction of the gel filtration treatment, and Lane F represents the agent of the present invention (4th Fraction of HA treatment). Numerals at the left represents molecular weights (KD) of the markers.

EXAMPLE

Practical embodiments of the present invention will be shown in the following examples, but the scope of the invention should not be limited thereto.

Example 1

Separation and purification of an infection-enhancing factor from armyworm larvae and properties of the agent (1) Production of entomopoxvirus in armyworm larvae Armyworm used in the experiment is the one which was subcultured in a cage with artificial feed mainly containing alfalfa powder, bran, agar, ebios or the like. Feeding was effected at 25° C., and light irradiation was adjusted to light time 16 hours and dark time 8 hours.

Entomopoxvirus pathogenic to armyworm (armyworm poxvirus) obtained from Wuhan Virus Research Laboratory in China in 1988 was used.

At first, armyworm larvae second instar were fed on small chips (200 mg/larvae) of artificial feed, into which an occlusion body suspension ($1 \times 10^8$ occlusion body/ml) was soaked, until the larvae consumed them. The larvae were further fed on fresh artificial feed. About 2 weeks later, the symptom of virus infection appeared in most of the larvae which arrived at final instar. (2) Purification of the occlusion body from the infected larvae Infected larvae were placed in a glass homogenizer and pulverized in 0.1M Tris-HCl buffer (pH 7.6) containing 2% ascorbic acid. The resultant mixture was filtrated through doubled gauze to remove debris, and the occlusion body was washed by conducting fractional centrifugation twice at 4° C. for 20 minutes at 2500×g, and the crude occlusion body obtained as precipitate was subjected to ultrasonication for 30 seconds with Sonifier (250 type, Branson Co., Ltd.) in 0.85% physiological saline containing 0.01M phosphate (pH 7.2) and 1% SDS. The occlusion body was again washed twice by fractional centrifugation at 2,500×g for 20 min at 4° C. The resultant precipitate was overlayed on the density gradient of Parcol (Pharmacia Company, pH 7.2) which had previously been prepared by centrifugal treatment at 22,000×g for 30 minutes. Centrifugal treatment with density gradient at temperature of 4° C. at 25,000×g, for 1 hour gave a band of purified occlusion body. This band was collected and subjected to fractional centrifugation twice at 2,500×g at temperature of 4° C. for 10 minutes with physiological saline containing phosphate buffer, and the precipitate was suspended in a small amount of distilled water to give a solution containing $5.5 \times 10^8$ occlusion body per ml. (3) Purification of infection-enhancing factor from the occlusion body An aqueous solution containing 0.6M sodium carbonate, 0.015M sodium thioglycolate and 0.03M ethylenediamine tetraacetate was mixed with the suspension of the occlusion body obtained above at ratio of 2:1 (V/V) and allowed to stand for 5 minutes at 25° C. to dissolve most of the occlusion body. The dissolving reaction was stopped by adding 3 volume of ice-chilled distilled water and subjected to high speed centrifugal treatment at temperature of 4° C. at 48,000×g for 30 minutes to precipitate the insoluble occlusion body and virus particles.

Figure 1:
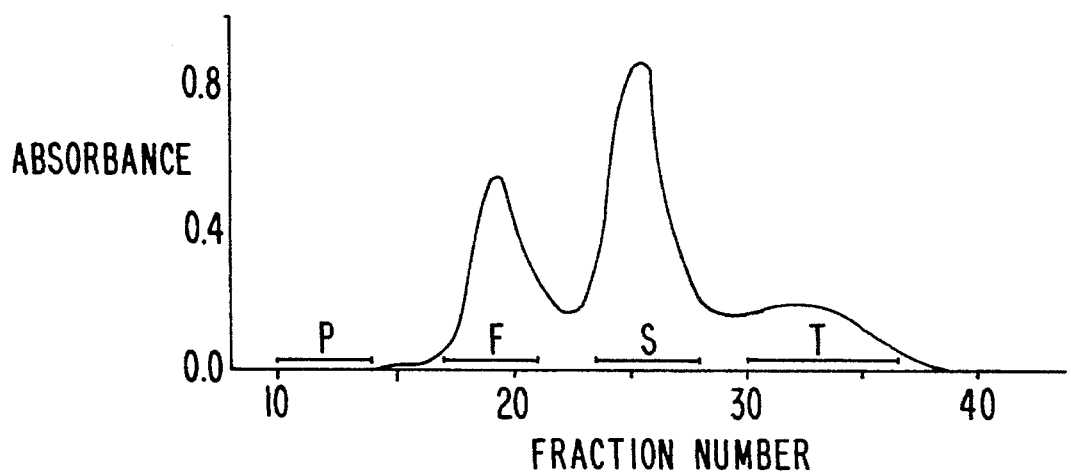
FIG. 1 shows the elution pattern of an alkali-dissolved occlusion body proteins in Sepharcryl column chromatography (See Example 1). In the figure, F, S and T show 1st, 2nd and 3rd Fractions, respectively.

The supernatant was subjected to Sephacryl column chromatography (Pharmacia Company, HR 200 type, 2.5×50 cm), eluting with 0.85% physiological saline containing 0.01M phosphate (pH 7.2) to give 3 fractions detected by UV at 280 nm (FIG. 1). Each fraction was collected, dialyzed to distilled water overnight, and the dialyzed solution was concentrated with a ultrafiltration system (Asahi Chemical Industry Co., Ltd.), and then subjected to assay for infection-enhancing activity. Each of three fractions was added to armyworm nuclear polyhedrosis virus, and the mixture was used to infect armyworm larvae (20 5th instar larvae) at virus concentration of $1.2 \times 10^5$ polyhedra/ml, and the infection rate was measured. Table 1 shows the results.

TABLE 1

| Treatment | First Test Infection Rate (%) | Second Test Infection Rate (%) |
|---|---|---|
| Polyhedra + 1st Fraction (F of FIG. 1) | 15 | 25 |
| Polyhedra + 2nd Fraction (F of FIG. 2) | 100 | 100 |
| Polyhedra + 3rd Fraction (F of FIG. 3) | 15 | 25 |

TABLE 1-continued

| Treatment | First Test Infection Rate (%) | Second Test Infection Rate (%) |
| --- | --- | --- |
| Polyhedra + Former Fraction | 15 | 25 |
| Polyhedra + Buffer | 15 | 25 |

Figure 2:
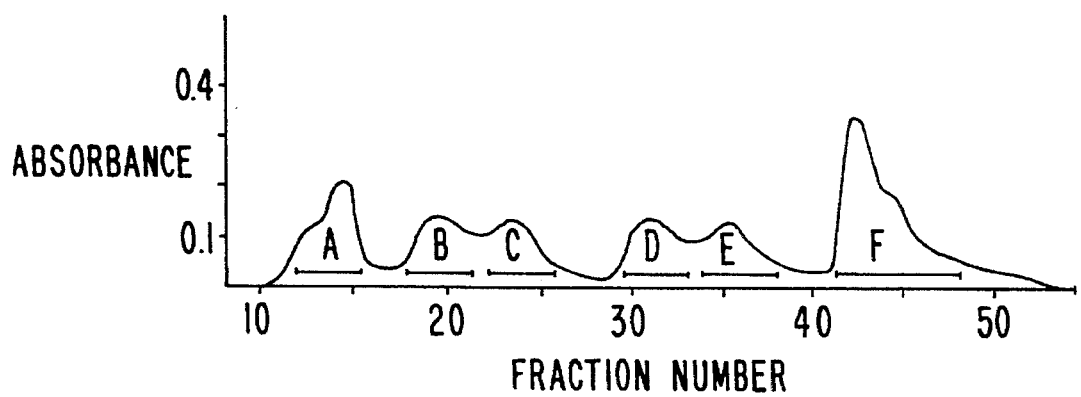
FIG. 2 shows the elution pattern of 2nd fraction in hydroxyapatite column chromatography, which was obtained in Sephacryl column chromatography in Example 1. In the figure, A, B, C, D, E and F show 1st, 2nd, 3rd, 4th, 5th and 6th Fractions, respectively.

The above result shows that only the 2nd fraction was active. The 2nd fraction was subjected to hydroxyapatite chromatography (Tonen Company), eluting with a gradient solvent of 0.001M to 0.1M phosphate buffer to give 6 fractions (FIG. 2). Each fraction was dialyzed and concentrated in the same manner as above, and the infection-enhancing activity was measured (Table 2).

TABLE 2

| Treatment | First Test Infection Rate (%) | Second Test Infection Rate (%) |
| --- | --- | --- |
| Polyhedra + 1st Fraction (A of FIG. 2) | 20 | 20 |
| Polyhedra + 2nd Fraction (B of FIG. 2) | 65 | 55 |
| Polyhedra + 3rd Fraction (C of FIG. 2) | 65 | 65 |
| Polyhedra + 4th Fraction (D of FIG. 2) | 60 | 65 |
| Polyhedra + 5th Fraction (E of FIG. 2) | 45 | 55 |
| Polyhedra + 6th Fraction (F of FIG. 2) | 15 | 15 |
| Polyhedra + Buffer | 15 | 15 |

Four fractions (2nd, 3rd, 4th and 5th fractions) showed the infection-enhancing activity. The components in these 4 fractions were subjected to amino acid composition analysis and peptide analysis, and any significant difference was not observed among these fractions. Accordingly, it seems that the components in these fractions are substantially the same and some of them underwent any modification during the course of purification, which gave four fractions. (4) Measurement of the purification degree of the infection-enhancing factor by column chromatography For the purpose of examining the purity of the infection-enhancing factor of the present invention at each purification step of Sephacryl column chromatography (Gel filtration) and hydroxyapatite chromatography (HA), protein concentration and the amount of protein causing 50% infection at each step were measured. For determining the amount for 50% infection, the polyhedra suspension was diluted with distilled water to obtain from 1 to 10 fold dilutions, and the 4 fold dilution was mixed with the purified agent of each step and used as an infection source. The mixture was quantitatively orally administered to 20 larvae (5th-instar) and infection rate was measured. Then, the amount of protein causing 50% infection was calculated from the infection rate. Table 3 showed the results.

TABLE 3

| Purification Steps (Sample Tested) | Protein Concentration (mg/ml) | First Test Amount of Protein causing 50% Infection (Polyhedra/Larvae) | Second Test |
| --- | --- | --- | --- |
| Before Purification (Protein of the Occlusion Body) | 2.12 | $10^{4.45}$ | $10^{4.50}$ |

TABLE 3-continued

| Purification Steps (Sample Tested) | Protein Concentration (mg/ml) | First Test Amount of Protein causing 50% Infection (Polyhedra/Larvae) | Second Test |
| --- | --- | --- | --- |
| Gel Filtration (2nd Fraction) | 0.47 | $10^{4.10}$ | $10^{3.80}$ |
| HA (4th Fraction) | 0.10 | $10^{4.24}$ | $10^{4.20}$ |

When the protein of the occlusion body was subjected to gel filtration and HA treatment, the amount of protein was found to be about ⅓ in each step, but the amount of protein causing 50% infection was almost unchanged. This results showed that the infection-enhancing activity per unit protein was increased to about 5 times through each step and to about 25 times through total steps. (5) Polyacrylamide gel electrophoresis of the infection-enhancing agent The infection-enhancing agent (4th Fraction from HA treatment) purified from armyworm poxvirus occlusion body was subjected to polyacrylamide gel electrophoresis according to Lemuli [Nature, 227, 680–685, 1970]. To a mixture of 2% SDS, 2% 2-mercaptoethanol and 20% glycerin was added an equal amount of aqueous solution of the infection-enhancing agent (1 mg/ml), and the mixture was heated at 100° C. for 3 minutes. After cooling, the mixture was applied on polyacrylamide gel and subjected to electrophoresis with a constant electric current of 30 mA. For determining the molecular weight, a Lawkit marker of Biorad Company was run in parallel on the same gel. As the result, only one band of 38 KD was detected and the molecular weight of the infection-enhancing agent was estimated to be about 38,000. FIG. 3 shows the SDS polyacrylamide gel electrophoresis pattern of the agent of the present invention.

In FIG. 3, Lane F represents the agent of the present invention (4th Fraction in HA treatment). In FIG. 3, Lane A represents the occlusion body, Lane B represents the occlusion body after alkali treatment, Lane C represents armyworm poxvirus particles, Lane D represents the particles after alkali treatment, and Lane E represents the 2nd Fraction in the gel filtration treatment. Main bands (110 KD and 55 KD) as seen in Lane A and main band (41 KD) as seen in Lane B are not observed in Lanes C and D. In Lane E, main band of 38 KD and other bands of 41 KD, 40 KD and 39 KD are observed and only 38 KD is observed in Lane F.

Furthermore, the purified infection-enhancing agent was subjected to isoelectric point electrophoresis under non-denatured conditions on polyacrylamide gel containing 5% Ampholine (Pharmacia Company), and the isoelectric point was found to be 3.8. In this test, eight standard proteins having isoelectric points from 2.4 to 5.6 were used as colored markers.

For comparison, the infection-enhancing agent isolated and purified from capsul of *Pseudaletia unipuncta* was subjected to electrophoresis in the same manner as above, and its molecular weight was found to be about 98,000. (6) pH and thermostability of the infection-enhancing agent The purified infection-enhancing agent was diluted with 4 volumes of buffer (0.05M phosphate buffer or 0.2M carbonate buffer). The resultant solution was divided into several portions, and each portion was adjusted to pH between 5.0 and 11.0 to obtain a series of sample solutions with pH interval of 0.5. The sample solutions were allowed to stand at 30° C. for 60 minutes, mixed with a suspension of polyhedra and the infection-enhancing activity was measured using armyworm larvae. No change of activity was found depending on pH change.

Next, the infection-enhancing agent was charged into tubular bottles, and the bottles were dipped in warm water at 60° C., 70° C., 75°, 80° C., 86° C. and 90° C. for 30 minutes, respectively. After cooling, the agent was mixed with a suspension of polyhedra and infection-enhancing activity was measured using armyworm larvae. No change of activity was found depending on the change of temperature up to 75° C.

Under the conditions of pH or temperature outside of the above-noted conditions, the infection-enhancing activity was lowered or completely disappeared. (7) Serological properties of the infection-enhancing agent The infection-enhancing agent was mixed with Freund's adjuvant and the mixture was injected to a rabbit in order to obtain antiserum. The reaction of the resultant antiserum with the infection-enhancing agent was assayed in 1% agar dissolved in 0.85% phosphate buffer (0.01M, pH 7.2)/physiological saline according to Micro Ouchterlony's method. A single precipitating line based on antigen-antibody reaction was formed.

The infection-enhancing agent isolated and purified from the capsul of *Pseudaletia unipuncta* was assayed in the same manner as above, but no precipitating line was found.

Example 2

Production of entomopoxvirus occlusion body in the cell line derived from armyworm The cell line derived from armyworm is a clone which was prepared by limiting dilution analysis from SIE-MSH-805 strain which was obtained from Shanghai Insect Research Laboratory in 1987. The cell line shows high susceptibility to entomopoxvirus (armyworm poxvirus). The medium used was TC/10 medium devised by Gardiner and Stockdeyl [J. Invertebr. Pathol., Vol.25, pp.35–46, 1975]. A plastic flask for closed culture system (Coning Company) was used as a culture vessal, and a standing culture was made at 26° C. Subculture was effected every 3–4 days in the manner as follows. At first, the cultured medium was mixed well to give a uniform concentration of cell suspension, which was transferred to a series of fresh vessels, and mixed with fresh medium to obtain about 4 fold dilution.

Body surface of the infected armyworm larvae obtained in Example 1 was sterilized with 70% alcohol and its body fluid was aseptically collected. The fluid was diluted 30 fold with the culture medium and centrifuged at 900×g for 10 minutes. Its supernatant was added to the culture at the ratio of 1% of the medium. Cell denaturing effect was observed 3 days after the inoculation and a lot of occlusion body was formed in most of the cells 7 days later. The supernatant of the cell culture thus obtained contained a lot of virus particles and used as an inoculating source.

The occlusion body was purified from the cultured cells in the same manner as in Example 1, and the infection-enhancing agent was isolated and purified. The agent was found to have the same physicochemical properties as that in Example 1.

Nuclear polyhedrosis virus can be a pathogen of harmful insects, and therefore, the virus has been utilized for eliminating and controlling harmful insects. The novel protein of the present invention provides economical biopesticides in combination with a sprinkling virus solution, since the protein enhances the infection of the nuclear polyhedrosis virus.

What is claimed is:

1. A method of enhancing the infection of an insect by nuclear polyhedrosis virus, which comprises orally administering to said insect an infection enhancing amount of an isolated protein having the following physicochemical properties:

(1) it has a molecular weight of about 38,000 on SDS polyacrylamide gel,
   (2) it has an isoelectric point of 3.8,
   (3) it is stable in a pH range of 5.5.–11.0,
   (4) it is stable at a temperature up to 75° C., and
   (5) it enhances the infection of said insect by said nuclear polyhedrosis virus.

2. The method of claim 1, wherein said protein is derived from the occlusion body of entomopoxvirus from infected army worms.

* * * * *

UNITED STATES PATENT AND TRADEMARK OFFICE
CERTIFICATE OF CORRECTION

PATENT NO. :
DATED      : 5,541,156
INVENTOR(S): July 30, 1996
             Toshihiko FUKUHARA It is certified that error appears in the above-indentified patent and that said Letters Patent is hereby corrected as shown below:

On the cover page, in item [73] Assignee: Please change "Mitsubishi Kasei Corporation" to --Mitsubishi Chemical Corporation--.

Signed and Sealed this

Eleventh Day of March, 1997

Attest:

BRUCE LEHMAN

*Attesting Officer*    *Commissioner of Patents and Trademarks*